Jan. 31, 1961 H. C. SWIM ET AL Plant Pat. 2,017
ROSE PLANT
Filed April 1, 1960
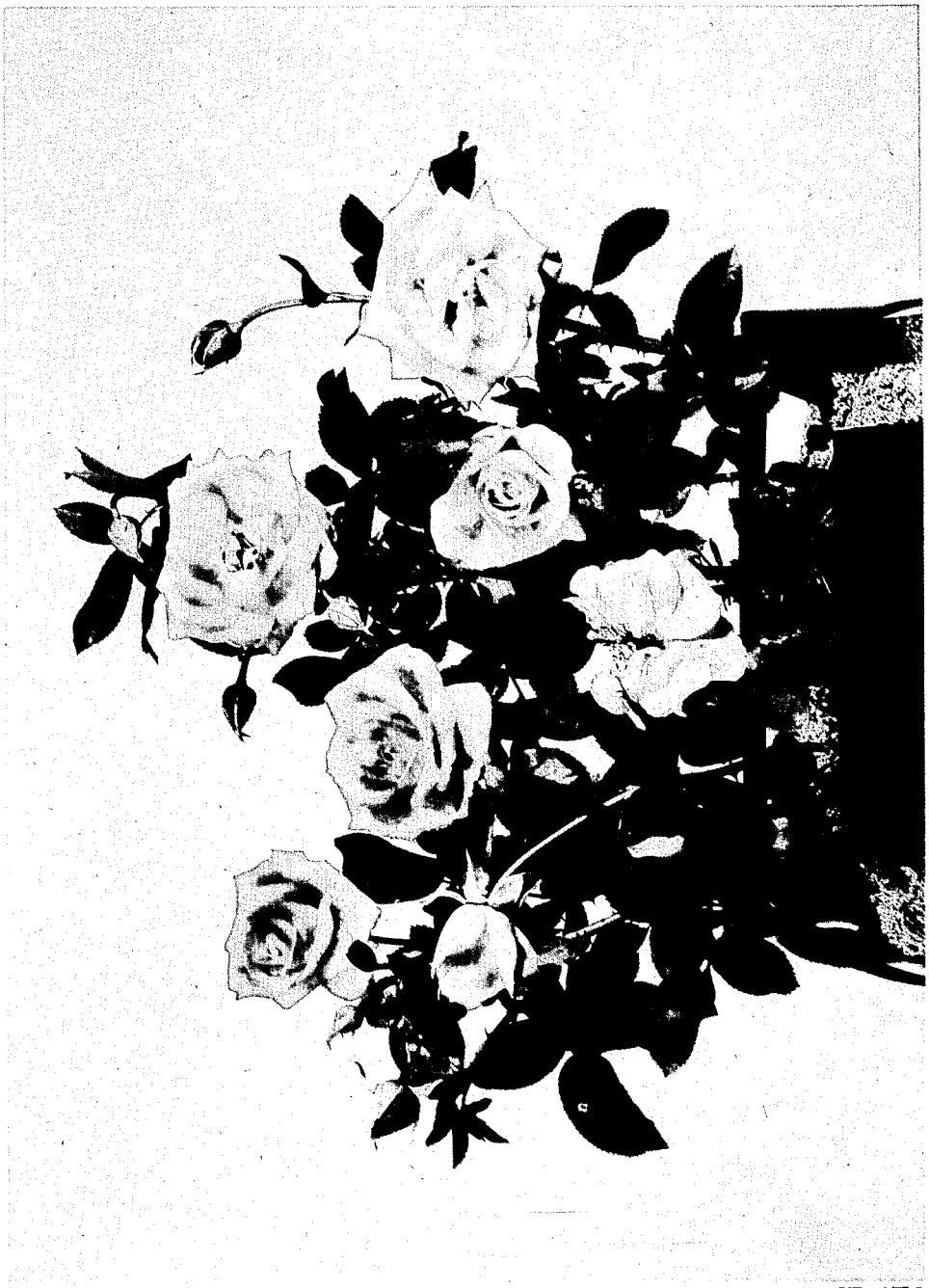
INVENTOR
H. C. Swim and O. L. Weeks
BY Robb & Robb
ATTORNEYS United States Patent Office Plant Pat. 2,017
Patented Jan. 31, 1961

2,017

ROSE PLANT

Herbert C. Swim, Ontario, and O. L. Weeks, Chino, Calif., assignors to The Conard-Pyle Company, West Grove, Pa., a corporation of Pennsylvania Filed Apr. 1, 1960, Ser. No. 19,436

1 Claim. (Cl. 47—61)

The present invention relates to a new and distinct variety of rose plant of the grandiflora class, which was originated by us by crossing the variety "Roundelay" (Plant Patent No. 1,280) with the variety "Crimson Glory" (Plant Patent No. 105).

As the result of this breeding, we have achieved a new rose variety which is endowed with the following unique and desirable combination of characteristics which are outstanding therein and which distinguish it from its parents, as well as from all other varieties of which we are aware:

(1) Large size and abundance of foliage comparable to that of the variety "Crimson Glory," combined with the heavy leathery texture comparable to that of the variety "Roundelay";

(2) Good resistance to powdery mildew disease comparable to that of "Roundelay";

(3) An excellent flower form, with broad petals, comparable to "Crimson Glory";

(4) An unusual brilliance and richness of the color of the inner surfaces of the flower petals which never before have been attained in rose flowers of the larger-flowered classes such as grandiflora and hybrid tea, said flower color being orange-red in general tonality; and (5) A substance and lasting quality of the flowers which is superior to either parent variety and equal to that of any other variety having comparable flower size.

In comparison with its seed parent, "Roundelay," the new variety does not grow as tall and is somewhat more spreading in its habit of growth, and while the flowers are classed as double, the flowers have fewer petals than those of this parent. The color of the flowers of the new variety may be described in popular terms as two-toned red, with the outer surfaces of the petals being dark red, while the inner surfaces are also red but dominated by orange, as distinguished from the more or less uniform dark red color of the flowers of the parent variety "Roundelay," in which no orange color is discernible.

As compared with its pollen parent, "Crimson Glory," the new variety is taller growing, its foliage is much more resistant to powdery mildew disease when grown under comparable environmental conditions in southern California, the flowers and the petals have substantially more substance (stiffness), with attendant longer lasting qualities, the flowers have only a slight fragrance as distinguished from the very fragrant flowers of "Crimson Glory," and the distinctive two-toned red flowers of the new variety is markedly distinguishable from the flower color of "Crimson Glory" to the same extent as in the case of the flowers of the seed parent "Roundelay."

Asexual reproduction of our new rose variety by budding, as performed at Chino, California, shows that the aforementioned characteristics and distinctions come true to form and are established and transmitted through succeeding propagations.

The accompanying drawing shows typical specimens of the vegetative growth and flowers of our new variety in different stages of development and as depicted in color as nearly true as it is reasonably possible to make the same in a color illustration of this character.

The following is a detailed description of our new variety, with color terminology in accordance with the Nickerson Color Fan, published by Munsell Color Company, Inc., of Baltimore, Maryland, except where general color terms of ordinary dictionary significance are obvious:

Type: Hardy; bush; outdoor; seedling; for cut flowers and for garden decoration.

Class: Grandiflora.

Breeding: Seedling.

*Seed parent.*—"Roundelay."

*Pollen parent.*—"Crimson Glory."

Propagation: Holds its distinguishing characteristics through succeeding propagations by budding.

*Flower*

Locality where grown and observed: Chino, California.

Flowers borne: Singly, as well as 2 or 3 or more to stem; in irregular clusters; on stems of normal strength and medium length.

Quantity of bloom: Free, outdoors.

Continuity: From intermittent to nearly continuous during growing season.

Fragrance: From none to slight.

Bud:

*Peduncle.*—From medium length to long; medium caliper; often bending, but sometimes erect; almost smooth; with few hair-like glands, but no prickles.

*Before calyx breaks.*—Size—medium. Form—ovoid; sometimes with a conspicuous neck; without foliaceous appendanges on the surface of the bud; occasionally with slender foliaceous parts extending beyond the tip of the bud equal to ¾ or more of its length. Color—near Dark Red, Plate 2.5R3/7.

*As calyx breaks.*—Color—from Dark Red, Plate 2.5R3/7 to Strong Red, Plate 5R4/12.

*As first petal opens.*—Size—from medium to large. Form—ovoid. Color: outside—Strong Red, Plate 5R4/12; inside—between Strong Reddish Orange, Plate 7.5R5/13, and Vivid Red, Plate 5R5/13, with outer areas overlaid with Dark Reddish Orange, Plate 7.5R4/11. Opening—opens up well.

Bloom:

*Size (when fully open).*—From medium to large; from 4 inches to 4½ inches.

*Petalage.*—Double from 28 to 40 petals, with from 3 to 6 petaloids; arranged regularly more or less.

*Form.*—High-centered at first, but becoming cupped; petals at first being cupped and remaining cupped at maturity.

Petals:

*Texture.*—Thick; leathery. Inside—velvety. Outside—satiny.

*Shape.*—Outside—nearly round. Intermediate—from obovate to slightly truncate. Inside—obovate—truncate.

This description of a newly opened flower was made from a rose grown outdoors at Chino, California:

*Color.*—Outer petal: outside surface—Strong Red, Plate 5R4/12; inside surface—Vivid Red, Plate 5R5/13, with overlay in areas touched by sunlight of Dark Reddish Orange, Plate 7.5R4/11, except for small spot around point of attachment which is Brilliant Yellow Green, Plate 2.5GY9/8, which in turn is sometimes surrounded by small irregular area of Moderate Red, Plate 2.5R4/10. Intermediate petal: outside surface—near Strong Red, Plate 5R4/12; inside surface—Vivid Red, Plate 5R5/13, with overlay in areas touched by sunlight of Dark Reddish Orange, Plate 7.5R4/11, except for small spot around point of attachment of Brilliant Yellow Green, Plate 2.5GY9/8, which in turn is sometimes surrounded by small irregular area of Moderate Red, Plate 2.5R4/10. Inner petal: outside surface—near Strong Red, Plate 5R4/12, except for midribs of white faintly overlaid with Moderate Red, Plate 2.5R8/5; inside surface—Strong Reddish Orange, Plate 7.5R5/13, overlaid with Dark Reddish Orange, Plate 7.5R4/11 over much of surface except at base where there is a small spear-shaped area pointed toward apex of Brilliant Greenish Yellow, Plate 7.5Y9/8.

This description was made from a rose that was grown outdoors but cut and allowed to open for three days indoor at Chino, California:

*Color.*—Outer petal: outside surface—between Strong Purplish Red, Plate 10RP4/12, and Deep Purplish Red, Plate 10RP3/10, except for small spot at point of attachment of Brilliant Yellow Green, Plate 2.5GY9/8; inside surface—near Moderate Red, Plate 2.5R4/10 at apex and at base, except for small area around point of attachment which is Brilliant Yellow Green, Plate 2.5GY9/8 and which in turn is surrounded by band of Deep Purplish Red, Plate 7.5RP3/9, with lateral margins near Strong Red, Plate 5R4/12. Inner petal: outside surface—between Strong Purplish Red, Plate 10RP4/12 and Deep Purplish Red, Plate 10RP3/10, except for small area about point of attachment which is Brilliant Yellow Green, Plate 2.5GY9/8; toward center of flower, the latter color extends along midrib well toward apex; inside surface—near Strong Red, Plate 2.5R5/12 in center of petal and at lateral margins; extending from apex along the margins to about ½ the distance to the base there is often a varying width of staining of Deep Purplish Red, Plate 10RP3/10; at base, a more or less spherical spot of Brilliant Yellow Green, Plate 2.5GY9/8 extends for about ⅛ inch up midrib, and somewhat more on innermost petals.

*General color effect.*—Newly opened flower—between Vivid Red, Plate 5R5/13 and Dark Reddish Orange, Plate 7.5R4/11. 3-days open—between near Strong Red, Plate 2.5R5/12 and near Moderate Red, Plate 2.5R4/10.

*Behavior.*—Persist; briefly fading purple; flower tends to become stained with purple in marginal area during cold and wet weather.

*Flower longevity.*—On bush in garden—4 days in October. Cut roses grown outdoors and kept at living room temperatures—4 days in October.

*Reproductive organs*

Stamens: Many; arranged irregularly about pistils; mixed with petaloids.

Filaments: From medium length to long; most with anthers. Color—whitish yellow at base, but reddish on upper ¾.

Anthers: From small to medium size; most open at once. Color—yellow.

Pollen: From moderate to abundant. Color—gold.

Pistils: Many.

Styles: Uneven; medium length; medium caliper; bunched.

Stigma: Color—white.

Ovaries: Most enclosed in calyx, but some protruding therefrom.

Hips: Short; ovoid; often with conspicuous neck; walls thick and fleshy. Color—deep orange at maturity.

Sepals: Permanent; moderate length; recurved.

Seeds: Many; from small to medium size.

*Plant*

Foliage:

*Leaves.*—Compound of 5 to 7 leaflets; abundant; from medium to large size; moderately heavy and leathery.

*Leaflets.*—Shape—ovoid, with apex acute. Base—rounded. Margin—both simply and doubly serrate.

*Color.*—Impossible to accurately described the foliage color due to the fact that the colors green, gray, blue and yellow are blended in the leaves in such a way that the colors cannot be compared with those found in the reference color chart and, therefore, the following color descriptions pertaining to the foliage should be considered as mere approximations. Mature: upper surface—between Dark Yellowish Green, Plate 2.5G3/3 and Moderate Olive Green, Plate 5GY4/3; under surface—near Strong Bluish Green, Plate 2.5BG5/9. Young: upper surface—shades of brown, purple and red, but probably closest to Dark Red, Plate 2.5R3/7, although somewhat darker; under surface—between Deep Purplish Red, Plate 10RP3/10 and Dark Red, Plate 2.5R3/7.

*Rachis (the supporting stem of the compound leaf).*—Medium caliper. Upper side—grooved. Under side—smooth, except for an occasional prickle.

*Stipules.*—Short; narrow; with short points usually recurved toward the stem.

*Disease resistance.*—Under field and garden conditions at Chino, California, this variety has good resistance to mildew as compared with the average rose varieties now available in commerce and when grown under comparable conditions.

Growth:

*Habit.*—Bushy; spreading; much-branched.

*Growth.*—Vigorous.

*Canes.*—Heavy.

*Main stems.*—Color—near Moderate Olive Green, Plate 2.5GY4/3. Large prickles—many; some short, medium and long; straight; with short, medium wide base; color—brown. Small prickles—from several to many; color—brown. Hairs—none.

*Branches.*—Color—near Moderate Olive Green, Plate 2.5GY4/3. Large prickles—many; from medium length to long; straight; with short, narrow base; color—brown. Small prickles—from several to many; color—brown. Hairs—few; color—brown.

*New shoots.*—Color—near Moderate Yellow Green, Plate 5GY5/6, overlaid or washed with anthocyanin of increasing intensity toward tip of new growth. Large prickles—many; long; straight; with short, narrow base; color—reddish purple. Small prickles—few; color—purple. Hairs—none.

We claim:

A new and distinct variety of rose plant of the grandiflora class, substantially as herein shown and described, characterized particularly as to novelty by the unique combination of large size and abundance of foliage, said foliage having a heavy and leathery texture, good resistance to powdery mildew disease, an excellent flower form, said flowers having broad petals, an unusual brilliance and richness of the color of the inner surface of the flower petals, with the color corresponding to orange-red in general tonality, and a superior substance and lasting qualities of the flowers.

No references cited.